(12) United States Patent  
Meehan et al.

(10) Patent No.: US 9,023,419 B2
(45) Date of Patent: May 5, 2015

(54) POROUS COATINGS FOR ORTHOPEDIC IMPLANTS

(71) Applicant: Hitemco Medical Application Inc., Old Bethpage, NY (US)

(72) Inventors: Michael Meehan, Melville, NY (US); Jinlong Wang, Flushing, NY (US); John Whalen, Huntington, NY (US); Edwin Garafalo, Massapequa, NY (US); Rick Montalbano, Miller Place, NY (US)

(73) Assignee: Hitemco Medical Application Inc., Old Bethpage, NY (US)

( * ) Notice: Subject to any disclaimer, the term of this patent is extended or adjusted under 35 U.S.C. 154(b) by 0 days.

(21) Appl. No.: 13/679,703

(22) Filed: Nov. 16, 2012

(65) Prior Publication Data

US 2013/0131824 A1    May 23, 2013

Related U.S. Application Data

(60) Provisional application No. 61/561,516, filed on Nov. 18, 2011.

(51) Int. Cl.
*A61K 6/083* (2006.01)
*B05D 3/10* (2006.01)
*B05D 3/12* (2006.01)
(Continued)

(52) U.S. Cl.
CPC . *C23C 4/12* (2013.01); *C23C 4/127* (2013.01); *A61F 2/28* (2013.01); *A61F 2/30767* (2013.01); *A61F 2/3094* (2013.01); *A61F 2002/3092* (2013.01); *A61L 27/06* (2013.01); *A61L 27/306* (2013.01); *A61L 27/56* (2013.01);
(Continued)

(58) Field of Classification Search
USPC ............................................... 427/2.24, 2.26
See application file for complete search history.

(56) References Cited

U.S. PATENT DOCUMENTS 4,542,539 A * 9/1985 Rowe et al. ................ 623/23.57
4,784,159 A * 11/1988 Szilagyi ....................... 607/116
(Continued)

FOREIGN PATENT DOCUMENTS

| WO | WO-2011-004217 | | 1/2011 |
| WO | WO 2011004217 A1 | * | 1/2011 |
| WO | WO-2011-126757 | | 10/2011 |

OTHER PUBLICATIONS

International Search Report for PCT/US2012/065576, Mar. 14, 2013, 3 pages.
Written Opinion for PCT/US2012/065576, Mar. 14, 2013, 6 pages.

*Primary Examiner* — Cachet Sellman
(74) *Attorney, Agent, or Firm* — Reising Ethington P.C.

(57) ABSTRACT

A high-purity porous metal coating is formed over a substrate by thermal spraying a metal coating material over the desired portion of the substrate in an atmospheric air environment. The metal coating material may react with the atmosphere to cause impurities in the applied coating. The impurity-rich portion of the applied coating is subsequently removed to form the high-purity porous metal coating. Process steps are included that cause the impurity-rich portion of the applied coating to be a surface portion that is removable to arrive at the high-purity coating. A protective shroud may be used to limit the amount of impurity imparted to the applied coating and/or a getter material may be employed to continually bring impurities toward the surface of the coated substrate during coating.

15 Claims, 5 Drawing Sheets

(51) Int. Cl.
*B05D 1/08* (2006.01)
*C23C 4/00* (2006.01)
*C23C 4/12* (2006.01)
*A61F 2/28* (2006.01)
*A61L 27/06* (2006.01)
*A61L 27/30* (2006.01)
*A61L 27/56* (2006.01)
*C23C 4/06* (2006.01)
*C23C 4/18* (2006.01)
*A61F 2/30* (2006.01)

(52) U.S. Cl.
CPC .. *C23C 4/06* (2013.01); *C23C 4/18* (2013.01); *A61L 2420/02* (2013.01); *A61L 2430/24* (2013.01)

(56) References Cited

U.S. PATENT DOCUMENTS

| | | | |
|---|---|---|---|
| 5,344,494 A | * | 9/1994 | Davidson et al. ............... 134/7 |
| 5,807,407 A | | 9/1998 | England et al. |
| 6,605,818 B1 | * | 8/2003 | Cornog et al. ............ 250/518.1 |
| 2004/0102854 A1 | | 5/2004 | Zhu |

* cited by examiner

POROUS COATINGS FOR ORTHOPEDIC IMPLANTS

CROSS-REFERENCE TO RELATED APPLICATIONS

This application claims the benefit of U.S. Provisional Ser. No. 61/561,516 filed on Nov. 18, 2011, the entire contents of which are incorporated herein by reference.

TECHNICAL FIELD

The present disclosure relates generally to porous coatings for use with orthopedic implants and methods for applying the coatings.

BACKGROUND

Orthopedic implants are sometimes fabricated to include porous surfaces or surface treatments that allow bone tissue to form within the porous structure after implantation and help fuse an implant with the bone to which it is attached. Material selection for such implants has been somewhat limited by the particular combination of desirable material properties, such as high tensile strength, fatigue strength, strength-to-weight-ratio, flexibility, toughness, wear resistance, and biocompatibility. Some of these material properties must also be taken into consideration when selecting surface treatments and the types of processes used to apply surface treatments. Where surface treatments include coatings, it may also be important to select implant and coating materials and processes that are capable of forming high strength bonds with each other. Certain thermal spraying methods may be used to apply coatings to orthopedic implants. But some of these methods may tend to impart impurities to the resulting coating, particularly where the coating material is reactive with atmospheric gases at high temperatures.

SUMMARY

In accordance with one embodiment, a method of forming a porous metal coating over a substrate, comprises the steps of: (a) providing a substrate and a metal coating material; (b) thermally spraying the metal coating material over a surface of the substrate in an atmospheric air environment to form an applied coating that includes an impurity-rich portion; and (c) removing the impurity-rich portion of the applied coating to form the porous metal coating. The porous metal coating has a chemical composition substantially the same as the metal coating material.

In accordance with another embodiment, an orthopedic implant includes a substrate and a porous coating over at least a portion of the substrate. The coating has a porosity that is greater than about 35%.

In accordance with another embodiment, a plasma spray coating process, comprises the steps of: (a) feeding a powder material into a plasma jet that is directed toward a substrate to form a coating over the substrate, wherein the powder material is reactive with atmospheric gases to form impurity compounds; (b) providing an inert gas shroud that surrounds the plasma jet and impinges the substrate during step (a); and (c) removing a surface portion of the coating.

In accordance with another embodiment, a method of forming a porous metal coating over a substrate, comprises the steps of: (a) thermally spraying at least one layer of a metal coating material over a surface of a substrate in an atmospheric air environment; (b) thermally spraying at least one layer of a getter material over the same surface of the substrate after step (b) in the atmospheric air environment to form an applied coating that includes an impurity-rich portion; (c) removing the impurity-rich portion of the applied coating to form the porous metal coating, wherein the porous metal coating has a chemical composition substantially the same as the metal coating material.

DESCRIPTION OF THE DRAWINGS

One or more embodiments will hereinafter be described in conjunction with the appended drawings, wherein like designations denote like elements, and wherein.

DETAILED DESCRIPTION

As will be apparent from the following description, porous surfaces can be formed on orthopedic implants using processes that include thermal spraying techniques. These processes can result in high-purity coatings without the added expense, longer cycle times, higher temperatures, or safety concerns sometimes associated with the use of vacuum chambers. While some embodiments described in conjunction with the figures are shown as femoral or humeral stems for use as portions of hip or shoulder replacements, any type of orthopedic implant may benefit from the teachings presented herein, including various components of structures designed to replace portions of knees, vertebrae, teeth, fingers, toes, or any other skeletal component.

Figure 1:
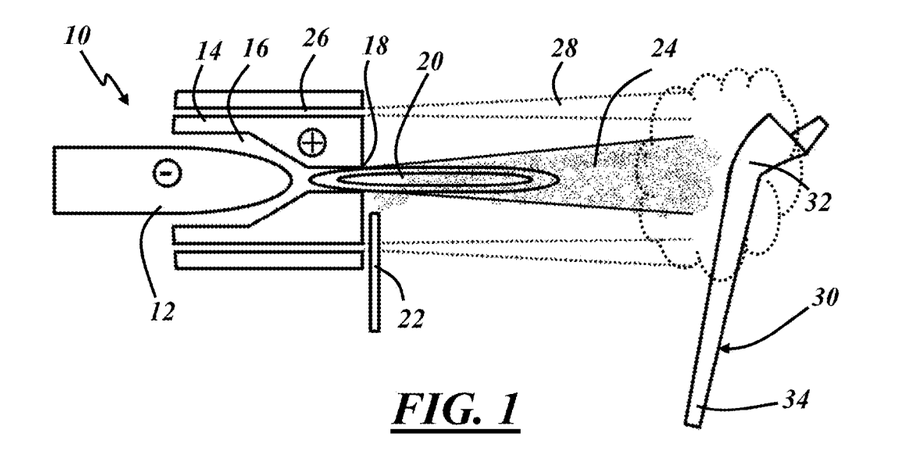
FIG. 1 is a schematic view of an exemplary plasma spray process, depicting a plasma spray gun shown in cross-section and an orthopedic implant component substrate being coated.

Referring to FIG. 1, a schematic view of an orthopedic implant coating process is shown, including a thermal spray gun directing a coating material toward a substrate for coating deposition. In this particular embodiment, the thermal spray gun is a plasma spray gun 10 and is shown coating an orthopedic implant component substrate 30. Only a front portion of the spray gun 10 is shown, and it is shown in a cross-sectional view taken through the center of its generally round shape. The illustrated spray gun 10 includes a cathode 12 and an anode 14. At least a front end of the cathode 12 is disposed within a portion of the anode 14 with an annular gap 16 formed therebetween. A plasma-forming gas flows through the gap 16 and toward nozzle 18. In operation, the plasma-forming gas is dissociated and ionized as it flows between the oppositely charged electrodes 12, 14 and past the point where an arc is formed between the electrodes. A very high temperature plasma jet or flame 20 is thus formed, extending from nozzle 18 and generally away from the gun 10. Some non-limiting examples of plasma-forming gases include argon, helium, hydrogen or their mixtures.

A coating material feeder 22 is arranged to supply the desired coating material to the plasma jet 20. In this embodiment, the coating material is provided in powder form through feeder 22, which is a shown as a supply line or conduit. The powder material can flow through and out of the conduit 22 along with an inert carrier gas. Feeder 22 can be part of the spray gun 10, or it can be separate from the spray gun. When the coating material is delivered to the plasma jet 20, it is rapidly heated and accelerated away from the gun and toward the substrate 30. Depending on several process parameters and the coating material composition and form, the coating material 24 is in a softened or molten state when it impacts the substrate 30, where a combination of high impact energy and temperature cause the coating material particles 24 to spread and bond to the surface of the substrate or to previously deposited coating material. Feeder 22 may also be provided to supply a getter material to the plasma jet 20, as will be described in more detail below.

Some coating materials are reactive with the surrounding environment, especially at the high coating process temperatures associated with plasma spray coating and some other thermal spray coating techniques. For example, oxides, nitrides, carbides, hydrides, or other compounds may be formed when the heated coating material reacts with the surrounding atmosphere either before or after the material is deposited over the substrate. Depending on the end use of the coating, some of these compounds may be considered impurities in the coating. Additionally, the coating material properties can be significantly affected by the inclusion of such impurities. In the case of titanium-based coating materials, for example, this normally ductile coating material can become brittle when even small amounts of these types of impurities are present, making the coating prone to cracking, fatigue failure, or otherwise affecting its overall properties.

As shown in FIG. 1, inert gas shielding may be used to help minimize or eliminate the formation of such impurities during the process. In the illustrated embodiment, shielding gas feeder 26 is in the form of a line or channel as part of the spray gun 10. In this embodiment, feeder 26 is a generally annular channel arranged so that axial fluid flow surrounds the nozzle 18. Feeder 26 may also comprise a series of discrete channels and/or spaced openings at the front end of spray gun 10 that are arranged about nozzle 18. An inert gas such as argon or helium may be routed through feeder 26 so that it is expelled in the same general direction as plasma jet 20, thereby forming a protective shroud 28 that helps separate the plasma jet 20 and the coating material 24 from the surrounding atmosphere. The protective shroud 28 shown in FIG. 1 is in the form of a high velocity curtain of inert gas that is substantially continuous about the plasma jet 20 and the propelled coating material 24. This tube-like gas shroud extends from the front end of the spray gun 10 to the substrate 30 that is being coated. Though FIG. 1 does not explicitly show the shroud 28 extending completely to the substrate, the shielding gas generally flows at a rate high enough to impinge the substrate surface, where the shielding gas is redirected in multiple directions to form an inert gas cloud or inert gas-rich environment at the area of the substrate being coated. This is only one example of a protective shroud. The protective shroud may also include a portion of solid material, such as a tubular extension extending from the front end of spray gun 10 and surrounding the plasma jet 20. In such an embodiment, a gas portion of the shroud may extend from the free end of the extension to the substrate being coated.

It should be understood that the plasma spray gun 10 and process set-up shown in FIG. 1 is non-limiting and may be varied in numerous ways. For example, the coating material feeder 22 may be arranged in an axial direction with its material-expelling end directed toward the plasma jet 20 and/or within the shroud 28; the shielding gas feeder 26 can be a separate component attached to the front of spray gun 10 and/or include radial channel portions; or the coating material can be in a form other than powder, such as in larger granules, in solid wire form, or at least partially liquid. These are only a few of the possible variations. In one embodiment, the shielding gas is the same as the plasma-forming gas, and may be provided from the same source or from different sources. In one particular embodiment, both the shielding gas and the plasma-forming gas include argon, and one or both gases may consist essentially of argon. Though the use of protective shroud 28 may lessen or eliminate the need to perform thermal spraying processes such as plasma spraying in a reduced pressure environment or vacuum, the above-described process may be performed in a partially evacuated chamber and may still provide certain benefits, such as the ability to use a lower vacuum level (higher chamber pressure).

Figure 2:
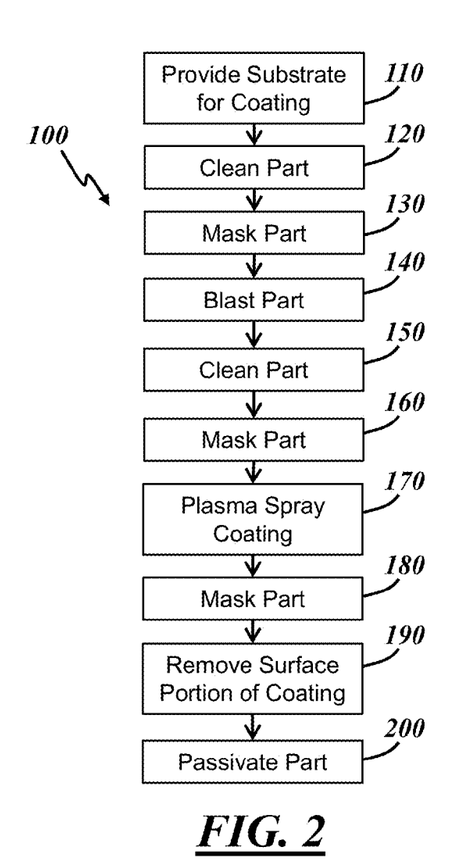
FIG. 2 is a process flow diagram of one embodiment of a plasma spray coating process.

Turning now to FIG. 2, a process flow diagram is shown that depicts an example process 100 for producing a component having a high-purity porous coating. The illustrative process generally includes the steps of providing a substrate for coating (step 110), spraying a coating over a desired portion of the provided part (step 170), and removing a surface portion of the coating (step 190). In one embodiment, the substrate provided in step 110 is an orthopedic implant component substrate, such as a femoral or humeral stem, but may also be any other type of substrate. Such orthopedic implant substrates are preferably constructed from metal materials, such as titanium or its alloys, stainless steel alloys, cobalt-chromium (Co—Cr) alloys, tantalum alloys, zirconium alloys, or other metals. One example of a suitable titanium-based material is commercially pure (CP) titanium. Examples of different grades of CP titanium are specified in ASTM F67 as grades 1-4. One example of a suitable titanium alloy is a titanium-aluminum-vanadium (Ti—Al—V) alloy. In one embodiment, the Ti—Al—V alloy is Ti—Al6-V4, or Ti-6-4, which includes 6% aluminum and 4% vanadium and is sometimes referred to as grade 5 titanium alloy. The substrate is not limited to a single material and may include portions formed from different materials. In some embodiments, the substrate may be constructed at least partially from a polymeric material, such as PEEK or UHMWPE.

As shown in FIG. 2, one or more additional steps may be performed prior to the step of spraying the coating (step 170). For example, the substrate may be cleaned (step 120) to remove any dirt, debris, oils, or other substances from prior manufacturing operations. The substrate may be masked (step 130) and blasted (step 140) to further clean and/or roughen portions of the substrate surface. For example, a portion of the substrate surface may be at least partly defined for blasting by masking the remainder of the substrate surface. The blasting may be performed at the same portion of the substrate that will be subsequently coated, thereby roughening the substrate to promote bonding between the coating and substrate. Blasting may also be performed on other portions of the substrate to provide a roughened surface for other reasons, or to remove sharp edges or other substrate defects. The blasting media may include white aluminum oxide or other suitable substance capable of roughening or removing surface layers of the given substrate material. The substrate may then be cleaned again (step 150) to remove any residue from the blasting operation in preparation for coating. This cleaning step may use pressurized air or other suitable fluid.

Figure 3:
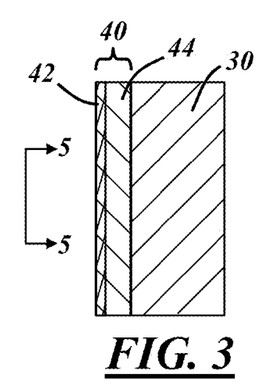
FIG. 3 is an cross-section of a portion of a coated substrate, where the coating is applied in an inert gas shielded plasma spray process.

Step 170 includes plasma spraying a coating over at least a portion of the substrate, in this embodiment. In embodiments where only a portion of the substrate is to be coated, the substrate may be masked (step 160) prior to plasma spraying to at least partly define the coating area or region. Alternatively, the entire substrate may be coated by omitting the masking step, or in embodiments where a clean line of demarcation is not necessary or desired where the coated and uncoated substrate meet, the coating may be selectively applied without masking. In one embodiment, the substrate is the femoral or humeral stem of FIG. 1 having a proximal end 32 and a distal end 34, and the substrate 30 may be masked so that a portion of the substrate near the proximal end 32 is coated. Though plasma spraying may be preferred with certain substrate and coating materials, other thermal spraying techniques may be used in some applications, such as combustion thermal spray processes, arc wire thermal spray processes, or HVOF thermal spray processes. Step 170 may include providing a protective shroud around the coating material during spraying, such as the inert gas shroud 28 depicted in FIG. 1. Such a shroud can be provided with plasma spraying or any other type of thermal spraying. Step 170 can be performed in an ambient atmosphere and may be referred to as air plasma spraying (APS) where plasma spraying is employed. The physical structure and composition of the applied coating is discussed in greater detail below.

Where APS or other thermal spraying methods are used to apply the coating material over the substrate in air and with a protective shroud as described above, some reaction with the surrounding atmosphere may still occur. For example, when the spraying step is complete, the temperature of the coating material may still be very high—i.e., high enough that oxides, nitrides, or other compounds of the coating metal will form at or near the surface of the coating. The resulting coating may have a structure similar to that shown in FIG. 3, where applied coating 40 includes a surface portion 42 over an underlying portion 44. Surface portion 42 includes oxides, nitrides, etc. from reaction with the atmosphere after the spraying is complete. Underlying portion 44 has a chemical composition that is substantially the same as the coating material that was fed to the spray gun. Thus, the protective shroud may not entirely eliminate the impurity compounds in the applied coating. But it can limit such compounds to the surface portion 42 or outer layer of the applied coating 40, whereas thermally spraying a coating onto the substrate in air without the protective shroud would result in the impurity compounds being included throughout the thickness of the applied coating.

Since the impurity compounds are limited to the surface portion of the applied coating, they can be eliminated by removal of the surface portion as in step 190. In one embodiment, the coated substrate may be masked again (step 180) and blasted with abrasive media that is capable of removing the surface portion. This is of course only one method of removing the surface portion, as it may also be machined, ground, or otherwise cut away from the applied coating. In one embodiment, large peaks or protruding solidified coating material are mechanically removed by striking, filing, cutting, or other means prior to blasting the applied coating. Where blasting media is utilized, it is preferable that the media is soluble in a fluid that the component is subsequently subjected to. For example, if the component is subsequently cleaned in an aqueous solution, it is preferable that the blasting media be water soluble. In one embodiment, the blasting media is soluble in a nitric acid or other acidic solution so that any residue on the component can dissolve and thus be removed in a subsequent passivation step. One example of a suitable blasting medium is MCD 300-180 or other MCD medium available from Himed (Old Bethpage, N.Y.). Other types of soluble blasting media include salts of sodium or other alkali metals. In orthopedic applications, a soluble blasting compound that is calcium-based may be preferred so that any residue that is not dissolved or otherwise removed from the finished component is similar in composition with bone tissue.

Removal of the surface portion in step 190 exposes a high-purity porous coating having substantially the same chemical composition as the coating material supplied to the spray gun in step 170. Thus, an APS process may be used without the expense and complications associated with a vacuum chamber to produce an orthopedic implant or other component with a high-purity porous coating, such as a titanium-based coating. Titanium-based coatings are traditionally difficult to apply outside of a vacuum chamber due to their very high melting temperature and high reactivity with atmospheric gases, especially in powder form where particle surface area is very high. The high-purity coating may then be passivated (step 200) by immersing the component in a nitric acid solution or other solution that promotes surface oxidation of the particular coating material. The passivation step forms a very thin and uniform layer of metal oxide at the coating surface, which is different from the oxidized surface portion removed in step 190 that is non-uniform, includes other impurity compounds, and is not limited to a very thin surface layer.

According to another embodiment, a method of forming a porous metal coating over a substrate may generally include the steps of thermally spraying a metal coating material over a substrate surface, thermally spraying a getter material over the same substrate surface, and removing an impurity-rich portion of the resulting coating. More particularly, the metal coating material and the getter material are sprayed over the same portion of the substrate surface so that at least some of the sprayed getter material overlies both the substrate and a previously applied layer of metal coating material. This embodiment is consistent with the above-described method in that the metal coating material and the getter material may be the same material in some instances. As used herein and in the context of thermally sprayed coatings, a getter material is a material that is capable of absorbing and/or reacting with environmental contaminants or impurities present in underlying coating layers. For example, an applied coating may be formed by thermally spraying one or more materials over a substrate in multiple layers or passes. Each pass builds up additional coating thickness. Any applied layer may include environmental impurities such as oxygen, nitrogen, hydrogen, carbon, etc. in the form of compounds of the thermally sprayed material(s). A subsequently applied getter material, thermally sprayed over a layer having environmental impurities, can absorb and/or react with the contaminants in the underlying layer, thereby purifying the underlying layer. As additional layers or passes of getter material are thermally sprayed, each subsequently applied layer purifies the underlying layer or layers by pulling the impurities toward the surface of the overall coating as it is being applied.

The getter material performs its purifying function by being present in a more highly reactive state with the impurity or impurities than the underlying layer. In other words, a newly applied layer of getter material competes with the underlying coating material for the impurity constituents. In one embodiment, the more highly reactive state is due to the newly applied layer being at a higher temperature than the underlying layer. In another embodiment, the more highly reactive state is due to the impurities being more reactive with the getter material than with the underlying coating material, whether due to a temperature difference or the relative reactivity of the impurities with each material or both. The getter material of this exemplary method may be the same material as the metal coating material, or the two materials may be different. In one example, a single material composition is thermally sprayed over the substrate in multiple layers, with each subsequently applied layer after the first layer acting as a getter material for the underlying layer(s). In one particular embodiment, the single material composition is titanium or a Ti-alloy. As each subsequent layer of the titanium-based coating material is applied and is present at a higher temperature than the underlying layer (which has cooled between passes), each subsequent layer acts as a getter material, absorbing any environmental impurities away from the underlying layer, thereby increasing the purity of the underlying layer and its mechanical properties.

The getter material function is useful even in embodiments that employ a protective shroud around the material being thermally sprayed, as some environmental contaminants may still be present. The resulting applied coating includes an impurity-rich surface portion, as with the previously described methods, and may be removed as described above. In another embodiment, the metal coating material comprises titanium, zirconium, tantalum, or any mixture thereof, and the getter material comprises a different one of these constituents or a different mixture of them. For example, a titanium-based material may be thermally sprayed over the substrate, followed by a tantalum-based getter material that purifies the titanium-based material. In this example, the impurity-rich surface portion includes a tantalum-based material with oxides, nitrides, or other tantalum-based impurities and is removed to arrive at the desired high-purity porous titanium-based coating. In another example, the thermally sprayed material is changed during the thermal spraying process from CP titanium to a titanium alloy or some other less pure titanium-based material so that the impurity-rich surface portion that is subsequently removed is formed from a less expensive material. Any material that is reactive with the impurities present during thermal spraying of the desired final coating material may be used as the getter material, so long as it is applied in a more highly reactive state with the impurities than is the underlying material.

The above-described processes are of course only examples of suitable coating processes. Additional steps may be included and/or certain steps may be omitted. For example, additional coating layers may be applied before or after thermal spray coating, such as a hydroxyapatite top coat or an interlayer of material that is compatible with both the coating material and the substrate material.

Various types and mixtures of materials can be used as the coating material or the getter material. For orthopedic implants having porous coatings, the coating material preferably includes titanium or titanium alloys, but may also be any of the previously listed metal substrate materials or ceramic or cermet materials. In one embodiment, the substrate material is Ti-6-4 and the coating material is CP titanium. While possibly advantageous to at least partially match coating and substrate constituents to promote coating-to-substrate bonding, the substrate and coating may be dissimilar. For example, a Co—Cr alloy substrate may be coated with a titanium-based material such as CP titanium or Ti-6-4. The use of a protective shroud during the spraying step may be particularly suitable with APS coating materials that are easily oxidized at high temperatures or coating materials that have material properties that are detrimentally affected by the inclusion of oxides or other compounds that can be formed from the surrounding atmosphere, such as titanium and its alloys.

In embodiments where the coating or getter material is introduced to the thermal spraying process as a powder, the particle shape, size, and size distribution may be varied to produce the desired coating properties and porous structure. For example, powder particles may be generally spherical or rounded, or they may be irregular in shape. For some materials, such as titanium-, tantalum-, or zirconium-based materials, irregularly shaped particles can be produced directly from sponge source material by crushing or otherwise breaking the sponge material down to the desired particle sizes. The particle size distribution may be used to control the pore structure of the finished coating to some degree. For example, a large particle size distribution can produce a coating with a correspondingly large pore size distribution, whereas a narrow particle size distribution can produce a coating with a more uniform pore size distribution. Whether the particle size distribution is large or small, the overall average particle size can affect the porosity of the finished coating. Smaller average particle sizes generally produce less porous coatings than larger average particle sizes, for example. The powder particle size may range from about 100 μm to about 500 μm. In one embodiment, the powder particle size ranges from about 180 μm to about 355 μm, where the range also represents the width of the particle size distribution. It has been found that utilizing powder particle sizes higher than about 180 μm can help to achieve higher coating porosity while maintaining other coating properties, such as wear and strength properties, in useful ranges. These ranges and preferred particle sizes may vary depending on process variables, coating material composition, or other factors.

Coating porosity, as used herein, refers to the percentage of open volume within the bulk coating. In other words, a given volume of the porous coating material includes solid coating material with voids distributed throughout the material. The porosity is the percentage of the overall volume that is void volume. The above-described process can produce coatings having a porosity in a range from about 20% to about 70%. The porosity may preferably range from about 50% to about 60%, or about 55% on average. This represents an increase over typical plasma sprayed coatings in orthopedic applications that have porosities in the 30-35% range. In such applications, where one purpose of the porosity is to provide void volume into which bone tissue can grow, higher porosity may be considered generally better where all other coating requirements, such as strength requirements, are met. Individual pore sizes may range from about 100 μm to about 1000 μm, and may preferable range from about 200 μm to about 300 μm. Whether the pore size distribution is large (e.g., from 100-1000 μm) or small (e.g., from 200-300 μm), the overall average pore size may preferably range from about 200 μm to about 300 μm, or approximately 250 μm.

Figure 4:
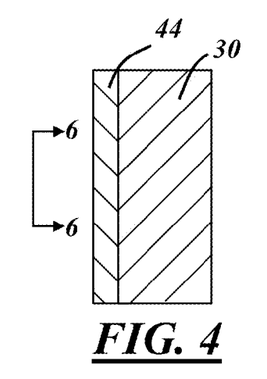
FIG. 4 is the cross-section of FIG. 3 after removal of a surface portion of the applied coating.

Depending on the intended application, the thickness of the finished porous coating can range anywhere from about 0.25 mm to about 5.0 mm. In certain orthopedic applications, the final coating thickness may preferably be in a range from about 0.5 mm to about 1.5 mm, though orthopedic applications may certainly utilize coating thicknesses outside this preferred range. In processes that include thermally spraying the coating over the substrate so that an impurity-rich surface portion is formed, additional coating thickness may be applied (e.g., during step 170 of FIG. 2) to facilitate removal of the surface portion to arrive at the high-purity porous coating of the desired thickness. In one embodiment, with reference to FIGS. 3 and 4, an orthopedic implant substrate is coated using an inert gas-shielded APS process, where the applied coating 40 has an overall thickness of about 1.0 mm and an impurity-rich surface portion 42 that is about 0.25-0.50 mm thick. In this embodiment, the finished porous coating thickness 44 is about 0.50-0.75 mm thick after removal of the surface portion. In another embodiment, the surface portion 42 is about one-third of the total thickness of the applied coating 40 so that the coating thickness after removal of the surface portion 42 is about two-thirds of the thickness of the applied coating 40. The thickness of the surface portion is not generally dependent on the applied coating thickness—i.e., the surface portion may generally range from about 0.05 mm to about 4.75 mm regardless of the total applied coating thickness or the desired final coating thickness. For example, the applied coating thickness may be up to about 5.0 mm with a surface portion having a thickness of up to about 4.75 mm, though it may be desirable to minimize the thickness of the surface portion to save material. In one embodiment, the surface portion has a thickness in a range from about 0.25 mm to about 1.5 mm, and may preferably have a thickness in a range from about 0.75 mm to about 1.5 mm.

Figure 5:
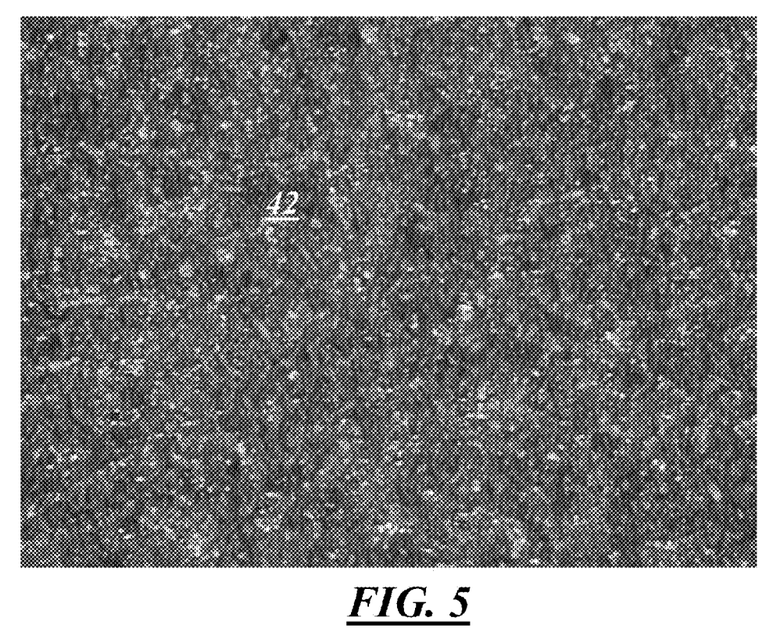
FIG. 5 is a magnified photographic image of an impurity-rich surface portion of a coating applied in an inert gas shielded plasma spray process.
Figure 6:
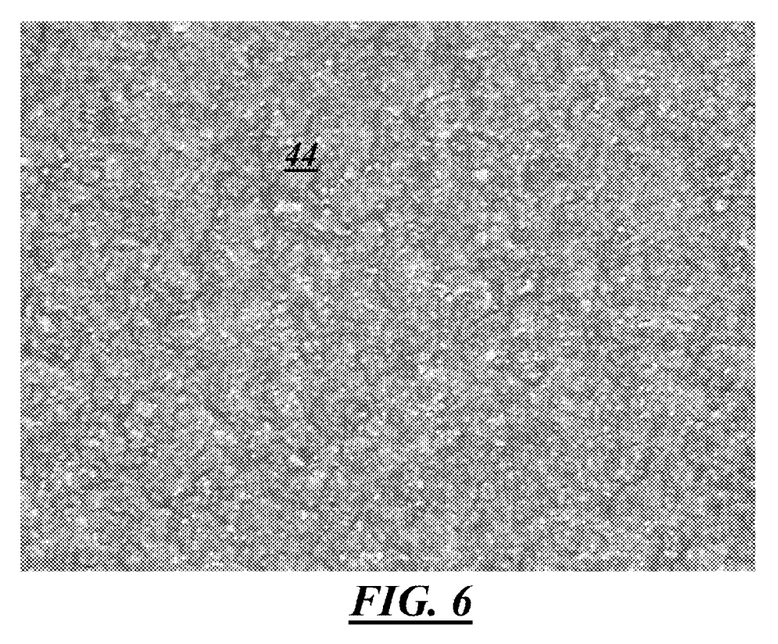
FIG. 6 is a magnified photographic image of the coating of FIG. 5 after the surface portion has been removed.

FIGS. 5 and 6 are magnified photographic images of the outer surface of a substrate coated using an inert gas shielded APS process. The substrate is Ti-6-4 and the coating material used in the APS process is CP titanium. FIG. 5 shows the outer surface, particularly the impurity-rich surface portion 42 of the applied coating. FIG. 6 shows the surface of the high-purity porous coating 44 that is exposed after removal of the surface portion 42. While structural differences may not be clearly apparent between the surfaces shown in the two images, the surface portion 42 shown in FIG. 5 is darker than the high-purity coating 44 shown in FIG. 6 due to the impurities. In other words, FIG. 6 visually appears like pure titanium in this case.

Figure 7:
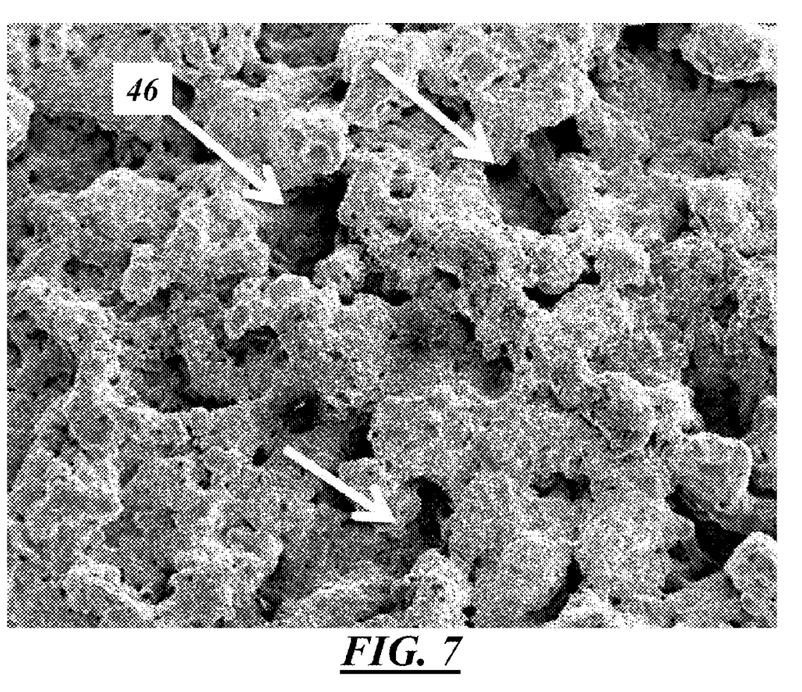
FIG. 7 is an SEM image of the porous coating of FIG. 6, formed by inert gas shielded air plasma spraying.
Figure 8:
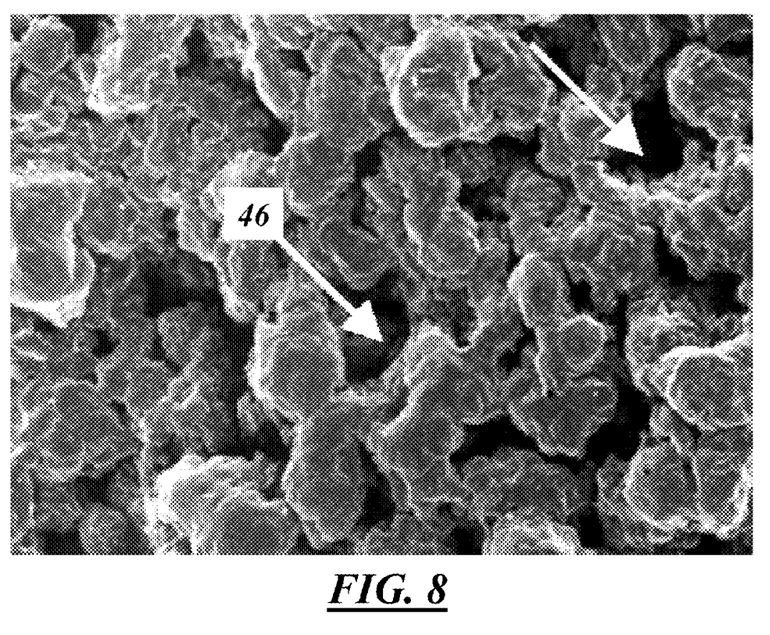
FIG. 8 is an SEM image of a porous coating formed by vacuum plasma spraying, for comparison with FIG. 7.

FIGS. 7 and 8 are SEM images of porous titanium-based coatings. The coating of FIG. 7 is applied by inert gas shielded APS, as described above, and the coating of FIG. 8 is applied by vacuum plasma spraying (VPS). These images show the similarity in the porous structure, or scaffolding, between the two plasma spraying techniques. The arrows are pointing to individual pores 46 in the coatings, indicating in-growth locations where bone tissue can grow into the coating after implantation, where the coating is part of an orthopedic implant.

Figure 9:
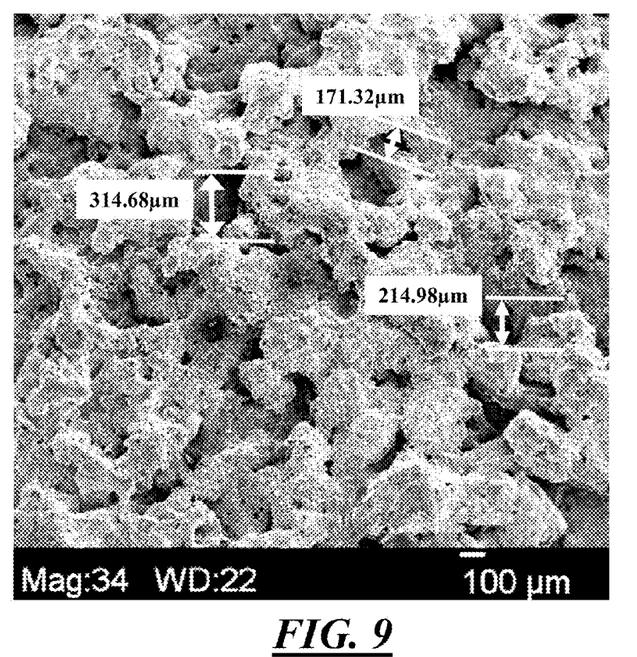
FIG. 9 is an SEM image of the porous coating of FIG. 6 with dimensions of some of the individual pores.
Figure 10:
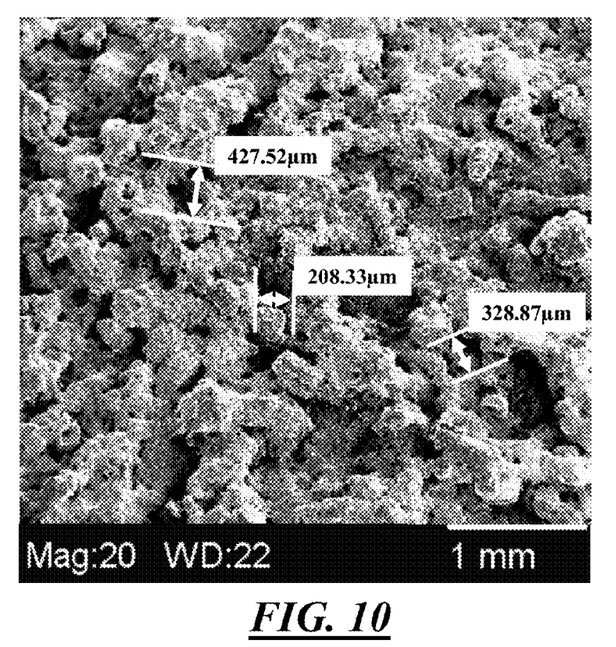
FIG. 10 is another SEM image of the porous coating of FIG. 6 with dimensions of some of the individual pores.

FIGS. 9 and 10 are SEM images of the porous titanium-based coating of FIG. 7 that was applied by inert gas shielded APS. These images include dimensions of some of the representative pores of the porous coating. The measured pores range in size from about 171 µm to about 428 µm, but are only examples, as it is apparent that larger and smaller pores are present in the coating and many of the pores may have their largest dimension in a plane other than the plane of the image.

Figure 11:
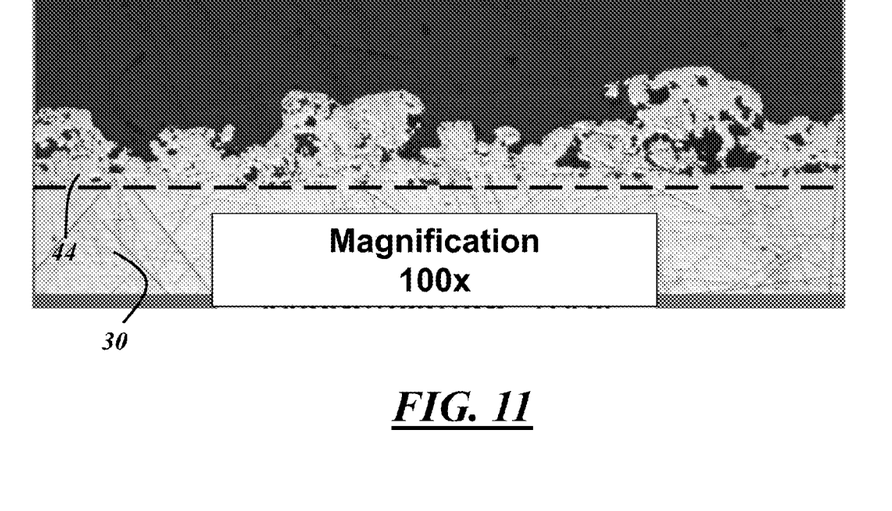
FIG. 11 is an SEM image of a cross-section of the porous coating of FIG. 6 and the underlying substrate.
Figure 12:
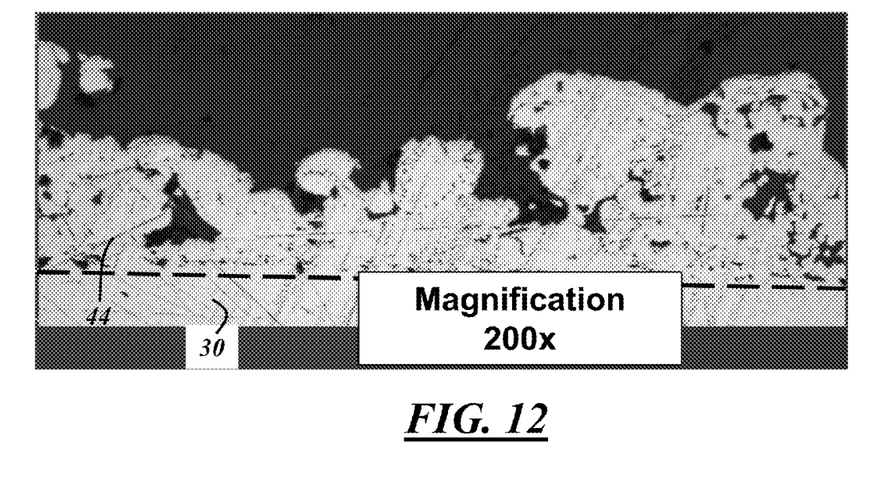
FIG. 12 is another SEM image of a cross-section of the porous coating of FIG. 6 and the underlying substrate, further magnified.

FIGS. 11 and 12 are SEM micrographs of cross-sections of a porous titanium-based coating applied by inert gas shielded APS. A dashed line is shown at the location where the coating 44 and substrate 30 meet. This location is approximate, as the coating and substrate that have undergone the above-described process are similar materials that are partially fused together at their interface.

Certain properties of the coatings shown in FIGS. 5-12 have been evaluated and are presented in TABLE I. CP titanium coatings were plasma sprayed onto Ti-6-4 substrates for these evaluations. As shown, the Tabor abrasion resistance of the shielded APS applied coating is comparable to the VPS applied coating. Abrasion resistance is well within the FDA guidelines, and is slightly more repeatable with the shielded APS process. The static tensile strength of the shielded APS coating is slightly lower, but more consistent, than that of the VPS coating, and well within the FDA guidelines. The static shear strength of the shielded APS coating is slightly higher and slightly more consistent than that of the VPS coating, and also well within the FDA guidelines.

TABLE I

| Test | FDA Guideline | VPS | Shielded-APS |
| --- | --- | --- | --- |
| Taber Abrasion, 100 cycles | 0.065 grams lost (max) | $0.031 \pm 0.012$ grams lost | $0.030 \pm 0.005$ grams lost |
| Static Tensile Strength | 3190 PSI (min) | $9957 \pm 1452$ PSI | $7823 \pm 449$ PSI |
| Static Shear Strength | 2900 PSI (min) | $5932 \pm 240$ PSI | $6510 \pm 155$ PSI |

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A method of forming a porous metal coating over a substrate, comprising the steps of:
   (a) providing a substrate and a metal coating material;
   (b) thermally spraying the metal coating material over a surface of the substrate using a thermal spray gun in an atmospheric air environment to form an applied coating that includes an impurity-rich portion;
   (c) providing a protective shroud around the metal coating material during step (b), wherein the protective shroud extends from the thermal spray gun to the substrate and includes an inert as such that the impurity-rich portion is a surface portion of the applied coating overlying a portion of the applied coating that has a chemical composition substantially the same as the metal coating material; and
   (d) removing the impurity-rich portion of the applied coating to form the porous metal coating, wherein the porous metal coating has a chemical composition substantially the same as the metal coating material.

2. The method of claim 1, wherein step (a) includes providing an orthopedic implant component substrate.

3. The method of claim 1, wherein the substrate of step (a) comprises titanium.

4. The method of claim 1, wherein the metal coating material comprises titanium.

5. The method of claim 1, wherein step (a) includes providing the metal coating material in the form of a powder.

6. The method of claim 5, wherein the powder has an average particle size of at least about 180 μm.

7. The method of claim 1, wherein step (b) includes air plasma spraying.

8. The method of claim 1, wherein the impurity-rich portion includes any combination of an oxide, a nitride, a hydride, or a carbide of the metal coating material as an impurity.

9. The method of claim 1, wherein step (c) includes blasting the impurity-rich portion with an abrasive media.

10. The method of claim 9, wherein the abrasive media is soluble in a passivation solution.

11. A method of forming a porous metal coating over a substrate, comprising the steps of:
(a) thermally spraying a first layer of a metal coating material over a surface of a substrate in an atmospheric air environment;
(b) thermally spraying at least one layer of a getter material over the same surface of the substrate after step (a) in the atmospheric air environment, wherein the getter material is present in a more highly reactive state with an impurity in the first layer of material to form an applied coating that includes an impurity-rich surface portion overlying a portion that has a chemical composition substantially the same as the metal coating material;
(c) removing the impurity-rich portion of the applied coating to form the porous metal coating, wherein the porous metal coating has a chemical composition substantially the same as the metal coating material.

12. The method of claim 11, wherein the metal coating material and the getter material are the same material.

13. The method of claim 11, wherein the metal coating material and the getter material are different materials.

14. The method of claim 11, wherein at least one of the materials comprises titanium.

15. The method of claim 11, further comprising the step(s) of:
providing a protective shroud around the metal coating material during step (a), providing a protective shroud around the getter material during step (b), or both.

\* \* \* \* \*